(12) United States Patent
Skarp et al.

(10) Patent No.: US 7,277,184 B2
(45) Date of Patent: Oct. 2, 2007

(54) METHOD OF CHARACTERIZATION OF LIQUID CRYSTAL CELL

(75) Inventors: Kent Skarp, Borlange (SE); Oleksandr Slobodyanyuk, Kiev (UA); Sergiy Valyukh, ul. Metrologichna 37-10, Kiev (UA) 03143

(73) Assignees: Swedish LCD Center, Borlange (SE); Sergiy Valyukh, Kiev (GB)

( * ) Notice: Subject to any disclaimer, the term of this patent is extended or adjusted under 35 U.S.C. 154(b) by 248 days.

(21) Appl. No.: 10/515,123

(22) PCT Filed: May 19, 2003

(86) PCT No.: PCT/UA03/00016

§ 371 (c)(1),
(2), (4) Date: Nov. 19, 2004

(87) PCT Pub. No.: WO03/098333

PCT Pub. Date: Nov. 27, 2003

(65) Prior Publication Data

US 2005/0219547 A1 Oct. 6, 2005

(30) Foreign Application Priority Data

May 20, 2002 (UA) ............................. 2002054098

(51) Int. Cl.
*G01B 9/02* (2006.01)

(52) U.S. Cl. ..................................................... 356/504

(58) Field of Classification Search ................ 356/503, 356/504, 517, 481
See application file for complete search history.

(56) References Cited

U.S. PATENT DOCUMENTS

| | | | | |
|---|---|---|---|---|
| 5,034,617 A | * | 7/1991 | Isobe | 250/559.28 |
| 5,502,564 A | * | 3/1996 | Ledger | 356/503 |
| 5,889,592 A | * | 3/1999 | Zawaideh | 356/504 |
| 5,943,134 A | * | 8/1999 | Yamaguchi et al. | 356/503 |
| 5,966,195 A | | 10/1999 | Sato et al. | |
| 6,081,337 A | | 6/2000 | Kwok et al. | |
| 6,545,763 B1 | * | 4/2003 | Kim et al. | 356/503 |
| 2004/0257567 A1 | * | 12/2004 | Woollam et al. | 356/369 |

FOREIGN PATENT DOCUMENTS

RU 2152588 7/2000
WO WO 00/43829 7/2000

OTHER PUBLICATIONS

Kucynski & Stryla; *Interference Method for the Determination of Refractive Indices and Birefringence of Liquid Crystals*; Mol. Cryst. Liq. Cryst., Gordon & Breach Science Publishers; 1975; vol. 31, pp. 267-273; Printed in Holland.

* cited by examiner

*Primary Examiner*—Hwa (Andrew) Lee
(74) *Attorney, Agent, or Firm*—James Creighton Wray; Clifford D. Hyra

(57) ABSTRACT

A method for simultaneous measuring a thickness of a liquid crystal layer and an average refractive index of the said liquid crystal in sealed liquid crystal cell is disclosed. The method is based on analysis of spectral positions of maxima and minima of interference oscillations, their magnitudes and their envelope in the spectrum of light mirrored by the liquid crystal cell at several different angles-of-incidence. The method is applicable to cells filled with different liquid crystals including cholesterics and smectics.

3 Claims, 3 Drawing Sheets

METHOD OF CHARACTERIZATION OF LIQUID CRYSTAL CELL

This application claims the benefit of Ukraine Application No. 2002054098 filed May 20, 2002 and PCT/UA03/00016, filed May 19, 2003.

BACKGROUND OF THE INVENTION

1. Technical Field

The present invention relates to a method for characterization of a liquid crystal cell, in particular for measuring a cell gap and an average refractive index of the liquid crystal in the cell. The method provided by the invention can also be applied to transparent thin films with properties similar to the liquid crystal layers.

2. Background Art

In the manufacturing process and in research and development of liquid crystal devices it is often necessary to know the liquid crystal cell gap and average refractive index.

The most simple and well-known prior art solution involves measuring the thickness of an empty cell i.e., cells prior to filling and sealing. For example the thickness may be calculated from interference of light reflected by the cell. However, the thickness of the filled cell can be different from an empty one.

A second method (for example U.S. Pat. No. 6,081,337) for determining the thickness of a liquid crystal layer is based on measuring an optical phase difference between the ordinary and extraordinary waves traveling through the liquid crystal layer. The thickness of the liquid crystal layer can then be calculated if the birefringence of liquid crystal is known. However, this method cannot be used to measure the cell gap of the liquid crystal cell if it is filled with the cholesteric liquid crystal. It is also necessary to know the birefringence a priori.

The closest prior art solution is based on the interference measurement of the optical path in the liquid crystal layer (W. Kuczynski and B. Stryla, "Interference Method for the Determination of Refractive Indices and Birefringence of Liquid Crystals", Mol. Cryst. Liq. Cryst., 1975, Vol. 31. pp. 267-273). According to this method, the liquid crystal located between two sub-mirror substrates is illuminated with light that has a broad spectrum, and the spectrum of reflected or transmitted light is measured. The optical path can be derived according the formula $$\Delta = dn = \frac{\lambda_1 \lambda_2}{2(\lambda_2 - \lambda_1)}, \lambda_2 > \lambda_1 \quad (1)$$

where d is the cell gap, n is a refractive index, $\lambda_1, \lambda_2$ are the wavelengths of two neighbor interference maxima or minima in the measured spectrum. The drawback of this method is the incapability to independently determine the cell gap d and the refractive index n.

DISCLOSURE OF INVENTION

The technical problem underlying the present invention is to provide a method for simultaneously measuring the cell gap and the average refractive index of the liquid crystal filled in the cell. The method according to the invention is based on the analysis of spectral features in spectra of cell light mirrored by the liquid crystal at several different angles-of-incidence. The features are spectral positions of maxima and minima of interference oscillations, their amplitudes and their envelope. This method is applicable to cells filled with different liquid crystals including cholesterics and smectics.

In order to achieve these objectives the method according to the present invention comprises the following steps:

transforming a liquid crystal in a cell under test to focal conic state (for cholesteric or smectic liquid crystals) or to isotropic state;

illuminating the liquid crystal cell under test with an obliquely incident beam from a light source with broad spectral emission;

measuring spectra of mirrored light of the liquid crystal cell at several different angles-of-incidence;

fixing spectral positions of features of interference oscillations and their envelope in the mirror reflected light spectra;

calculating the cell gap and average refractive index of the liquid crystal according to formulae provided in further description.

BRIEF DESCRIPTION OF DRAWINGS

These and other objectives and features of the present invention will become clearer from the following description taken in conjunction with the preferred embodiments, and with reference to the accompanying drawings in which.

DETAILED DESCRIPTION OF THE PREFERRED EMBODIMENTS

Mode for Carrying Out the Invention

This invention is capable of measuring both the cell gap and average refractive index of the liquid crystal.

Figure 1:
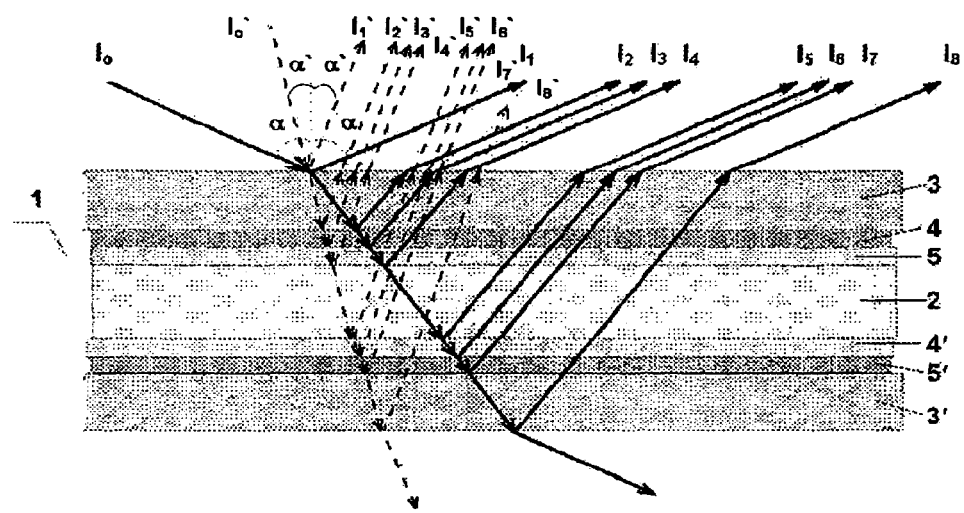
FIG. 1 shows light reflection by stratified structure of the liquid crystal cell.

FIG. 1 sketches light reflection from sandwiched structure of liquid-crystal cell 1. Layers in such a structure have different thickness and refractive indices. The liquid crystal layer 2 is characterized with the thickness d and the average refractive index n that for the liquid crystal material in the isotropic or focal conic state is $$n = \frac{1}{3}(n_o + 2n_e),$$

where $n_o$, $n_e$ are principal refractive indices of the liquid crystal. The liquid crystal layer 2 is placed between two glass plates 3 and 3', the outside surfaces of which contact with air and inner surfaces are covered with an alignment layer 4 and 4' and an electric conductive layer 5 and 5' that are transparent in the visible spectral range.

Typical the thickness d of the liquid crystal layer 2 is about 4-20 μm, the thickness of the glass plates 3, 3' is about 1-2 mm, the thickness of the layers 4, 4' and 5, 5' is about 0.05-0.1 μm and 0.02-0.05 μm, respectively. FIG. 1 is not to scale.

According to the invention a liquid crystal cell 1 in FIG. 1 is illuminated with a collimated light beam $I_0$. The angle-of-incidence is α. At each interface between the cell layers with different refractive indices a fraction of the incident beam is reflected. As a consequence the mirrored light consists of a plurality of beams with different phases and amplitudes labeled as $I_1 \ldots I_8$ in FIG. 1. Spectra of mirrored light from the liquid crystal cell are measured at several angles-of-incidence α' when cell 1 is illuminated with collimated light beam $I_o'$.

The intensity I of the light mirrored from the sandwiched structure of the liquid crystal cell can be found according to a well-known formula as a time averaged squared magnitude of the electric vector complex amplitude of the mirrored light field which is a sum of complex amplitudes of interfering beams $I_1 \ldots I_8$:

$$I = \overline{(\vec{E}_1 + \vec{E}_1 + \ldots + \vec{E}_8)(\vec{E}_1 + \vec{E}_1 + \ldots + \vec{E}_8)^*}, \quad (2)$$

where each complex amplitude $\vec{E}_k = |\vec{E}_k| e^{i\Phi_k}$ is a product of the magnitude $|\vec{E}_k|$ by an exponential phase multiplier $e^{i\Phi_k}$, where the phase relative retardation $\phi_k$ of the beam; the sign "*" means complex conjugation, the sign "¯" means the average over the time period that is much longer than the light oscillation period. The phase delays of the beams $I_1$ and $I_8$ reflected by external surfaces of the glass plates 3, 3' is very different from phase delays of the other beams reflected by the cell, due to the large thickness of the glass plates. This allows one to use the following expression for the intensity of light reflected by the cell:

$$I = I_1 + I_8 + \mathrm{Re}\left(\sum_{k=2}^{7}\sum_{m=2}^{7} \sqrt{I_k I_m}\, e^{i(\varphi_k - \varphi_m)}\right), \quad (3)$$

where $I_k$ is an intensity of the light reflected by the k-th interface. The phase delay $\phi_k$ is in direct ratio to the respective optical path in the layer $\Delta_k$: $\phi_k = 2\pi\Delta_k/\lambda$. According to this expression the phase delay $\phi_k$ depends on the wavelength that causes the appearance of the oscillation in the spectrum of reflected light. The positions of maxima and minima in the observed spectrum depend on the optical delays of the layers, and the magnitudes of the oscillation depend on the ratio of beam intensities $I_k$. The oscillation period in the spectrum, which appears as a result of interference of the beams $I_k$ and $I_m$, is in inversion proportion to the respective phase difference $\phi_k - \phi_m$. The phase difference between the beams reflected from the fore-interface (top) and back-interface (bottom) of a layer with thickness h and refractive index n is $$\phi_k - \phi_{k+1} = 2\pi\Delta_{k,k+1}/\lambda = 2\pi 2hn \cos\theta/\lambda, \quad (4)$$

where θ is an angle between the normal to the surface border and the light wave vector inside the layer, $\Delta_{k,k+1}$ is the optical path in the layer. For instance, the maximal optical delay $\Delta_{1,2}$ for a layer of the transparent electrode 5 with the thickness h=0.1 μm and with the refractive index n=2 in the visible range (0.4<λ<0.7 μm) reaches its maximum value 0.4 μm at normal incidence, and the respective phase difference changes from 1.14π up to 2π. So, the spectral distance between two neighboring maxima or minima of oscillation produced by interference of these beams is wider than the visible region. On the other hand, the liquid crystal layer, due to its greater thickness, causes the spectral intensity oscillations with period much less than the visible range.

Figure 2:
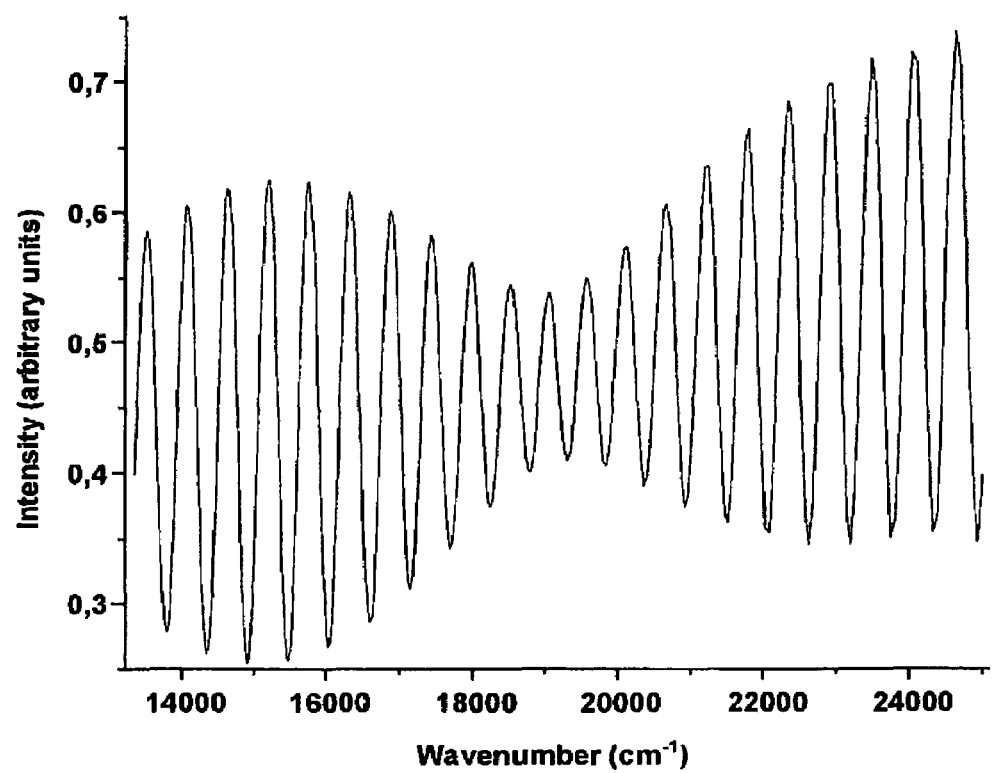
FIG. 2 shows interference oscillations in the spectrum of light mirrored by the stratified liquid crystal cell structure shown in FIG. 1.
Figure 3:
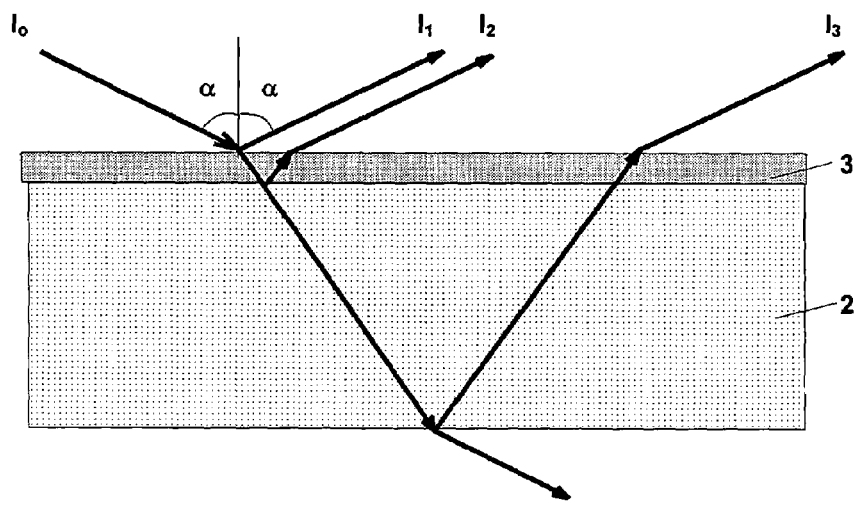
FIG. 3 is a scheme of light reflection by equivalent bi-layer model that provides the same interference oscillation (spectral positions of maxima and minima, wavelength dependence of oscillation amplitude and its envelope) in the mirrored light spectrum like in the mirrored light spectrum from the stratified liquid crystal cell structure shown in FIG. 1.
Figure 4:
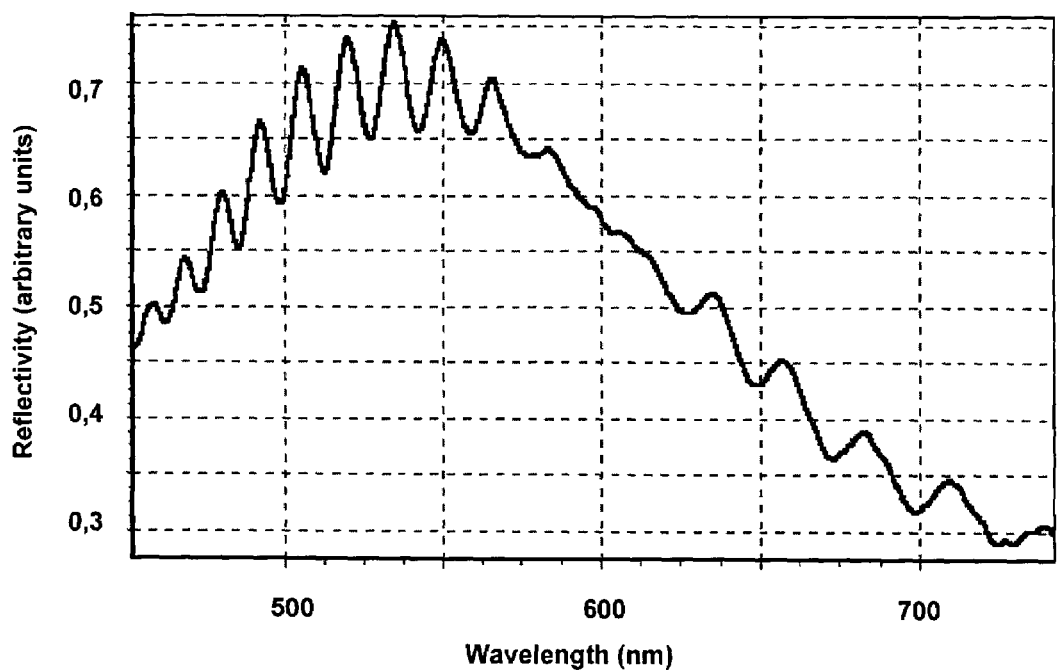
FIG. 4 is a graph illustrating a typical spectrum of the light mirrored by the liquid crystal cell.

After mathematical transformations, the expression for the intensity of the reflected light (3) can be written as:

$$I = a_0 \cos[(2\pi\Delta_{34})\nu] + A\cos[2\pi(\Delta_{34} + \Delta_\Omega)\nu] = \quad (5)$$
$$a_0 \cos[(2\pi\Delta_{34})\nu] + A\cos[(2\pi\Delta')\nu],$$

where $a_0$, A are numerical coefficients; $\Delta_{3,4}$ is the optical path difference between the beams reflected from the upper and lower interfaces of the layer of liquid crystal material 2; $\Delta_\Omega$ is the optical path difference due to reflections from interfaces of the thin layers, $\Delta_\Omega \ll \Delta_{3,4}$; and ν is a wavenumber: $\nu = 1/\lambda$. The sum of the two harmonic functions versus ν with close "frequencies" Δ and Δ' in the expression (5) leads to the well known phenomenon of beating, whereby the resulting intensity I(ν) can be given as a product of two harmonic functions of ν with essentially different "frequencies":

$$I(\nu) = A'(\nu)\cos[(2\pi\Delta)\nu], \quad (6)$$

where $A'(\nu) = A\cos[(\pi\Delta_\Omega)\nu]$ can be considered as an oscillation amplitude with a "frequency" Δ, which changes slowly according to harmonic law as can be seen in FIG. 2. Such intensity distribution in the spectrum is the same as the spectral intensity distribution of light reflected by an equivalent two-layer structure, as shown in FIG. 3, that provides the same interference maxima and minima in the spectrum of reflected light as the liquid crystal cell shown in FIG. 1. The above is confirmed by the measured spectrum shown in FIG. 4.

According to the invention, the characteristic points of dependency I(ν) are used for simultaneously determining the cell thickness d and the average refractive index n of liquid crystal material.

The wavelength $\lambda_{A\ max}$ that corresponds to the maximum amplitude, satisfies the condition:

$$\lambda_{A\ max} = \frac{2\tau}{k}, \quad (7)$$

where $$\tau = \frac{\Delta_\Omega}{2}, \quad k = 1, 2 \ldots,$$

and the wavelength $\lambda_{A\ min}$ that corresponds to the minimum amplitude, satisfies the condition:

$$\lambda_{A\ min} = \frac{4\tau}{2k-1}. \qquad (8)$$

Representing A through an incident angle $\alpha$, and taking into account the formulas (6-8), we obtain the conditions for wavelengths of maxima $\lambda_{max}$:

$$\frac{2d\sqrt{n^2-\sin^2\alpha}+\tau}{\lambda_{max}} = N, \qquad (9)$$

and wavelengths of minima $\lambda_{min}$:

$$\frac{2d\sqrt{n^2-\sin^2\alpha}+\tau}{\lambda_{min}} = \frac{2N+1}{2}, \qquad (10)$$

where N=0, 1, 2, . . . is the order of interference.

There are several ways to obtain d and n using the expression (9) or the expression (10), or both. For instance, the optical thickness can be calculated from the formula:

$$\Delta = \frac{m\lambda_{N+m}\lambda_N}{\lambda_{N+m}-\lambda_N} - \tau, \qquad (11)$$

where $\lambda_{N+m}, \lambda_N$ are wavelengths of two maxima (or minima) that separated by m−1 maxima (or minima). Then, after some transformations, we obtain:

$$n = \sqrt{\frac{\Delta_2^2\sin^2\alpha_1-\Delta_1^2\sin^2\alpha_2}{\Delta_2^2-\Delta_1^2}}, \qquad (12)$$

where $\Delta_1, \Delta_2$ are the optical paths that are obtained from the expression (11) for the angles $\alpha_1$ and $\alpha_2$, respectively. The geometrical thickness of liquid crystal cell d can be found from obtained n and $\Delta$ $$\left(d = \frac{\Delta}{n}\right).$$

In like manner, using the expression (12) one derives $$n \approx \sqrt{\frac{\lambda_2^2\sin^2\alpha_1-\lambda_1^2\sin^2\alpha_2}{\lambda_2^2-\lambda_1^2}}, \qquad (13)$$

where $\lambda_1, \lambda_2$ are the wavelengths of maxima (or minima) corresponding to the same interference order at the angles $\alpha_1$ and $\alpha_2$, respectively.

The dispersion of the refractive index n can be taken into account by Couchy's formula $$n = n_0 + \frac{n_1}{\lambda^2},$$

where $n_0$, $n_1$ are constants.

The conditions for maxima (9) can be rewritten as $$\sin^2\alpha = n^2 - \frac{(\lambda_{max}N-\tau)^2}{4d^2}. \qquad (14)$$

Similarly, the expression (10) can be represented as $$\sin^2\alpha = n^2 - \frac{(\lambda_{min}(0.5+N)-\tau)^2}{4d^2}. \qquad (15)$$

Figure 5:
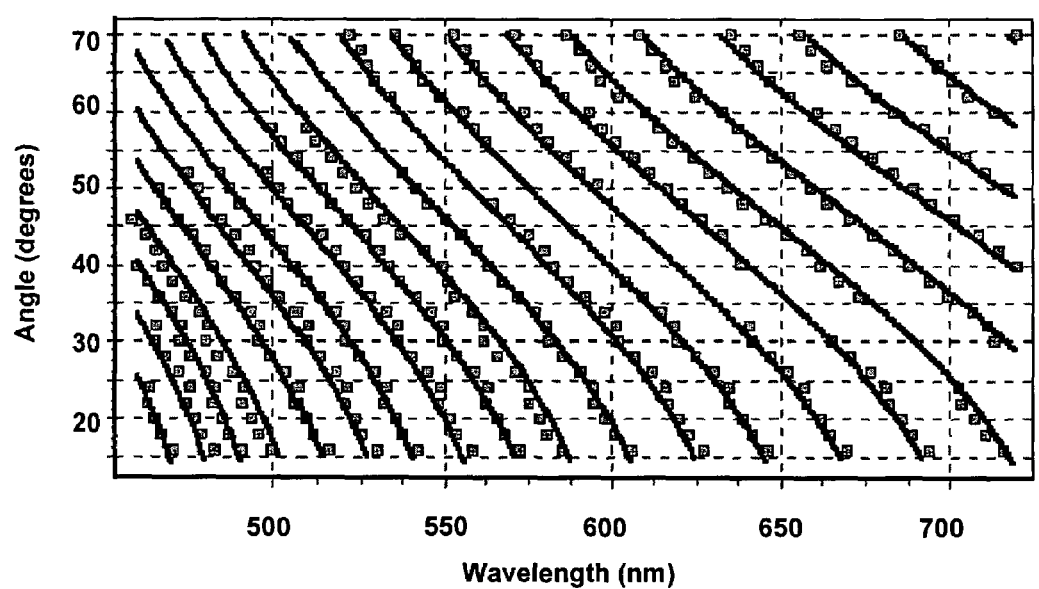
FIG. 5 shows the typical measured dependence of spectral positions of interference maxima (or minima) in mirrored light spectra versus angle-of-incidence (reflectance) and their fitting with polynomials according to the invention.

In order to increase the accuracy and authenticity of measurements by the disclosed method it is expedient to approximate the experimental obtained functions $\sin^2\alpha = f(\lambda_{min}, N)$ and $\sin^2\alpha = f(\lambda_{max}, N)$ with the polynomial $f = k_{-4}\lambda^{-4} + k_{-2}\lambda^{-2} + k_0 + k_1\lambda + k_2\lambda^2$. To calculate $n_0$, $n_1$ and d it is necessary to get the best fitting of the above mentioned functions (14) and (15) with variation of coefficients $k_i$ (i=−4, −2, 0, 1, 2). The experimental obtained spectral positions of oscillation maxima versus an angle-of-incident are shown by squares in FIG. 5, and the resultant approximation with polynomials is shown by solid curves. The experimental points are absent in the region where magnitude of spectral intensity oscillation is too small and ratio signal-to-noise is unacceptable.

It will be understood that the invention is not restricted to the aforedescribed and illustrated exemplifying embodiments thereof, and that these embodiments can be modified within the scope of the inventive concept illustrated in the accompanying Claims.

The invention claimed is:

1. A method for characterization of a liquid crystal cell, comprising:
   illuminating the front surface of the liquid crystal cell with an obliquely incident beam of light with continuous spectrum in broad spectral region,
   measuring a light spectrum mirrored by the liquid crystal cell,
   fixing spectral positions of features of interference oscillations in the mirrored light spectrum,
   and calculating the liquid crystal cell characteristics, wherein spectra of mirrored light from the liquid crystal cell are measured at several angles-of-incidence and the thickness of the liquid crystal cell and average refractive index of liquid crystal filling said cell are calculated from spectral positions of features of interference oscillations in the mirrored light spectra.

2. The method according to claim 1, wherein spectral positions of minimum amplitude of interference oscillation in the spectrum of light mirrored from the liquid crystal cell are additionally fixed and used to exclude an influence of the alignment layers and transparent electrodes of the liquid crystal cell on calculated values of thickness of the liquid crystal cell and average refractive index of the liquid crystal.

3. The method according to claim 1, wherein dependencies of measured spectral positions of interference maxima and minima versus an angle-of-incidence on the front surface of the liquid crystal cell are fitted with polynomials powers of wavelengths, and the best fitting values of polynomials coefficients are used to calculate the thickness of the liquid crystal cell and average refractive index of the liquid crystal.

* * * * *